| United States Patent [19] | [11] Patent Number: 4,559,081 |
| Van Gemert | [45] Date of Patent: Dec. 17, 1985 |

[54] SULFAMOYL UREA DERIVATIVES

[75] Inventor: Barry Van Gemert, Massillon, Ohio

[73] Assignee: PPG Industries, Inc., Pittsburg, Pa.

[21] Appl. No.: 677,617

[22] Filed: Dec. 3, 1984

[51] Int. Cl.$^4$ .................. C07D 407/12; A01N 43/66
[52] U.S. Cl. ......................................... 71/93; 544/212
[58] Field of Search ............................. 544/212; 71/93

[56] References Cited

U.S. PATENT DOCUMENTS 4,515,620 5/1985 Bohner ................................ 544/212

FOREIGN PATENT DOCUMENTS 15962 1/1983 Japan .
2110689 6/1983 United Kingdom .
2113217 8/1983 United Kingdom .

*Primary Examiner*—John M. Ford
*Attorney, Agent, or Firm*—Edward J. Whitfield

[57] ABSTRACT

The invention relates to herbicidally active sulfamoyl urea derivatives, including herbicidal formulations and uses thereof to control the growth of noxious plants, i.e., weeds.

5 Claims, No Drawings

SULFAMOYL UREA DERIVATIVES

FIELD OF THE INVENTION

This invention relates to herbicidally active sulfamoyl urea derivatives, including herbicidal formulations uses thereof to control the growth of noxious plants, i.e., weeds.

DESCRIPTION OF THE INVENTION

This invention concerns sulfamoyl urea derivatives represented by the Formula I:

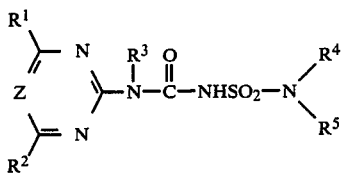
I.

wherein:
Z is =N or =CH;
$R^1$ and $R^2$ are the same or different and represent halogen or $C_1$ to $C_4$ alkyl, or alkoxy;
$R^3$ and $R^4$ are the same or different and represent hydrogen, $C_1$ to $C_4$ alkyl, alkoxyalkyl, haloalkyl, or up to $C_3$ alkenyl or alkynyl;
$R^5$ is

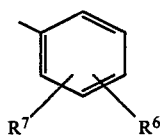

wherein:
$R^6$ is hydrogen or halogen;
$R^7$ is

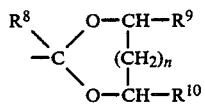

wherein
$R^8$ is $C_1$ to $C_3$ alkyl;
$R^9$ and $R^{10}$ are hydrogen or $C_1$ to $C_3$ alkyl; and
n is 0, 1, or 2.

It is, of course, to be understood that agronomically suitable cationic salts of the Formula I compounds are within the scope of this invention.

The Formula I compounds may conveniently be prepared by reacting a suitably substituted amino pyrimidine or amino triazine of the Formula II:

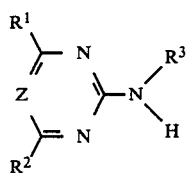
II.

wherein $R^1$, $R^2$, $R^3$ and Z are as previously defined, with a halosulfonyl isocyanate of the formula OC—N—SO$_2$—Hal, wherein Hal is halogen, e.g., chlorine, fluorine or bromine to form the corresponding halosulfonyl urea of the Formula III:

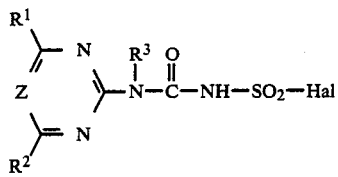
III.

The Formula III compound is then reacted with at least a stoichiometric amount of a suitably substituted amine of the Formula IV:

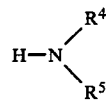
IV.

wherein $R^4$ and $R^5$ are as previously defined, to form a Formula I compound of the invention.

Preferred compounds of the invention are those wherein $R^3$, $R^4$ and $R^6$ are hydrogen, Z is =N, and n is 0. Preparation of a particularly preferred compound of the invention is illustrated by the following Example.

EXAMPLE

Preparation of:
1-[2-(1,3-dioxolan-2yl-methyl)phenylsulfamoyl]-3-(4-methyl,6-methoxy-1,3,5-triazin-2-yl)urea (a) To a round bottom flask was charged 10 grams of orthonitroacetophenone, 40 milliliters of ethylene glycol and 0.5 gram of p-toluene sulfonic acid. The stirred mixture was then heated to 140° C. with a nitrogen purge to remove water. After about 36 hours, HPLC indicated the reaction was over 90 percent complete. The mixture was cooled and suction filtered and the solid product was washed with aqueous sodium carbonate solution and suction dried affording 8 grams of white crystalline solid. The solid was taken up in a solution of methanol and aqueous sodium carbonate, transferred to a Parr shaker flask and 0.5 gram of palladium on charcoal was added. The mixture was hydrogenated at 50 psi for 2 hours, hydrogen uptake being complete at this point. The hydrogenated mixture was then filtered to remove catalyst and stripped of solvent on a rotary evaporator. The residue was then extracted with a mixture of water and methylene chloride. After phase separation, the organic phase was dried over anhydrous sodium sulfate and stripped on a rotary evaporator affording 7.0 grams of clear oil (which solidified on standing) which was identified by NMR analysis as 2-(1,3-dioxolan-2yl-methyl)aniline.

(b) To 150 milliliters of methylene chloride maintained at 0°–5° C. via an ice bath was added 1.41 grams (0.01 mole) of 4-methyl-6-methoxy-2-amino-1,3,5-triazine and 1.54 grams of chlorosulfonyl isocyanate. The mixture was stirred at ice temperature until all of the solid had dissolved and for an additional one-half hour after which a methylene chloride solution containing 0.01 mole of triethylamine and 0.01 mole of the amine prepared in part (a) of this Example were added dropwise, the mixture maintained at ice temperature throughout the addition. The mixture was permitted to rise to ambient temperature, recooled in the ice bath and poured into ice cold 2% aqueous hydrochloric acid where it was shaken and rapidly separated. The organic phase was washed with three portions of ice cold water and dried over anhydrous sodium sulfate. Evaporation of solvent afforded a pasty material that crystallized upon addition of a small amount of diethylether. Suction filtration afforded 2.6 grams of material identified by NMR analysis as the desired product, 1-[2-(1,3-dioxolan-2yl-methyl)phenylsulfamoyl]-3-(4-methyl-6-methoxy-1,3,5-triazin-2-yl)urea.

Although the invention has been illustrated by the foregoing Example with regard to the preparation of a specific compound within the scope of Formula I, it is to be understood that other compounds within the scope of Formula I may readily be prepared by those skilled in the art simply by varying the choice of starting materials and using the same or similar techniques.

Weed control in accordance with this invention is effected by applying to the soil prior to emergence of weeds therefrom or to the plant surfaces subsequent to emergence from the soil, a herbicidally effective amount of a compound of this invention. It is, of course, to be understood that the term "a compound of this invention" also includes mixtures of such compounds or a formulation containing a compound or mixture of compounds of this invention.

The term "herbicidally effective amount" is amount of a compound of this invention required to so injure or damage weeds such that the weeds are incapable of recovering following application, while not causing any substantial damage to any valuable crop amongst which the weeds might be growing. The quantity of a compound of this invention applied in order to exhibit such satisfactory herbicidal effect may vary over a wide range and depends on a variety of factors, such as, for example, hardiness of a particular weed species, extent of weed infestation, climatic conditions, soil conditions, method of application, and the like. Typically, as little as one or less pound per acre of a compound of this invention would be expected to provide satisfactory weed control, although in some instances application rates in excess of one pound per acre; e.g., up to 5 or more pounds per acre might be required. Of course, the efficacy of a particular compound against a particular weed species may readily be determined by routine laboratory or field testing in a manner well known to the art. It is expected that satisfactory weed control can be had at a rate of application in the range of 0.01 to 2.0 pounds per acre.

Of course, a compound of this invention can be formulated according to routine methods with any of several known and commonly used herbicidal diluents, adjuvants and carriers. The formulations can contain liquid carriers and adjuvants such as organic solvents, as well as emulsifiers, stabilizers, dispersants, suspending agents, spreaders, penetrants, wetting agents and the like. Typical carriers utilized in dry formulations include clay, talc, diatomaceous earth, silica and the like. Preferred formulations are those in the form of wettable powders, flowables, dispersible granulates or aqueous emulsifiable concentrates which can be diluted with water at the site of application. Also, dry formulations such as granules, dusts, and the like, may be used.

When desired, a compound of this invention can be applied in combination with other herbicidal agents in an effort to achieve even broader vegetative control. Typical herbicides which can be conveniently combined with Formula I compound include atrazine, hexazinone, metribuzin, ametryn, cyanazine, cyprazine, prometon, prometryn, propazine, simazine, terbutryn, propham, alachlor, acifluorfen, bentazon, metolachlor and N,N-dialkyl thiocarbamates such as EPTC, butylate or vernolate. These, as well as other herbicides described, for example, in the *Herbicide Handbook of the Weed Science Society of America,* may be used in combination with a compound or compounds of the invention. Typically such formulations will contain from about 5 to about 95 percent by weight of a compound of this invention.

The herbicidal formulations contemplated herein can be applied by any of several method known to the art. Generally, the formulation will be surface applied as an aqueous spray. Such application can be carried out by conventional ground equipment, or if desired, the sprays can be aerially applied. Soil incorporation of such surface applied herbicides is accomplished by natural leaching, and is of course facilitated by natural rainfall and melting snow. If desired, however, the herbicides can be incorporated into the soil by conventional tillage means.

Compounds of this invention are believed effective for preemergence or postemergence control of a wide variety of broadleaf and grassy weeds. Typical of the various species of vegetative growth that may be controlled, combated, or eliminated are, for example, annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, kochia, medic, ragweed, hemp nettle, spurrey, pondweed, carpetweed, morningglory, ducksalad, cheatgrass, fall panicum, jimsonweed, witchgrass, watergrass, wild turnip, and similar annual grasses and weeds. Biennials that may be controlled include wild barley, campion, burdock, bull thistle, roundleaved mallow, purple star thistle, and the like. Also controlled by the compounds of this invention are perennials such as quackgrass, Johnsongrass, Canada thistle, curly dock, field chickweed, dandelion, Russian knapweed aster, horsetail, ironweed, sesbania, cattail, wintercress, horsenettle, nutsedge, milkweed, sicklepod, and the like.

More particularly by way of example, the compound prepared in the Example was tested for preemergence and postemergence herbicidal activity by spraying a solvent solution of same on a variety of common broadleaf and grassy weed species, under controlled laboratory conditions of light, temperature and humidity. The extent of herbicidal injury was evaluated, periodically after application, and a Numerical Injury Rating (NIR) assigned on a scale of from 0 (no injury) to 10 (all plants dead). The following Table gives the NIR assigned to each weed specie (identified by common name) 22 days after preemergence and postemergence application of the compound of the Example at rates of 0.5 to 1.0 per acre:

| WEED | PREEMERGENCE | | POSTEMERGENCE | |
|---|---|---|---|---|
| SPECIES | 0.5 | 1.0 | 0.5 | 1.0 |
| Teaweed | 6 | 6 | 5 | 5 |
| Jimsonweed | 5 | 6 | 8 | 8 |
| Wild mustard | 8 | 8 | 8 | 10 |
| Yellow nutsedge | 10 | 10 | 6 | 7 |
| Yellow foxtail | 7 | 8 | 6 | 7 |
| Large crabgrass | 7 | 8 | — | — |
| Johnsongrass | 7 | 8 | 6 | 6 |
| Coffeeweed | 3 | 6 | 6 | 6 |

| WEED | PREEMERGENCE | | POSTEMERGENCE | |
|---|---|---|---|---|
| SPECIES | 0.5 | 1.0 | 0.5 | 1.0 |
| Velvetleaf | 5 | 5 | 8 | 8 |
| Tall morning-glory | 4 | 5 | 5 | 6 |
| Wild oats | 8 | 7 | 2 | 1 |
| Barnyard grass | 8 | 8 | 3 | 5 |
| Cotton | — | — | 4 | 1 |

Although the invention has been described in considerable detail by the foregoing, it is to be understood that many variations may be made therein by those skilled in the art without departing from the spirit and scope thereof as defined by the appended claims.

I claim:

1. A compound represented by the formula:

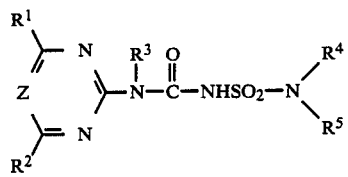

wherein:

Z is =N;

$R^1$ and $R^2$ are the same or different and represent halogen or $C_1$ to $C_4$ alkyl, or alkoxy;

$R^3$ and $R^4$ are the same or different and represent hydrogen, $C_1$ to $C_4$ alkyl, alkoxyalkyl, haloalkyl, or up to $C_3$ alkenyl or alkynyl;

$R^5$ is

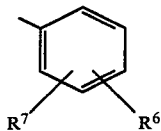

wherein:

$R^6$ is hydrogen or halogen;

$R^7$ is

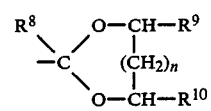

wherein:

$R^8$ is hydrogen or $C_1$ to $C_3$ alkyl;

$R^9$ and $R^{10}$ are hydrogen or $C_1$ to $C_3$ alkyl; and n is 0, 1, or 2.

2. A compound of claim 1 wherein $R^3$, $R^4$ and $R^6$ are hydrogen and n is 0.

3. A compound of claim 2 that is 1-[2-(1,3-dioxolan-2yl-methyl)phenylsulfamoyl]-3-(4-methyl-6-methoxy-1,3,5-triazin-2yl)urea.

4. A herbicidal formulation containing an agronomically acceptable carrier and a compound or mixture of compounds defined in claim 1.

5. In a method of controlling weeds wherein a herbicidally effective amount of herbicide is applied to a growth medium prior to emergence of weeds therefrom or to the weeds subsequent to their emergence from the growth medium, the improvement residing in using as the herbicide a compound or mixture of compounds defined in claim 1.

* * * * *